United States Patent
Gan et al.

(10) Patent No.: US 12,315,109 B2
(45) Date of Patent: May 27, 2025

(54) SYSTEMS AND METHODS FOR NEURAL-NETWORK BASED COLOR RESTORATION

(71) Applicant: Covidien LP, Mansfield, MA (US)

(72) Inventors: Xiaofang Gan, Shanghai (CN); Zhentao Lu, Shanghai (CN); Xiao Li, Shanghai (CN)

(73) Assignee: Covidien LP, Mansfield, MA (US)

( * ) Notice: Subject to any disclaimer, the term of this patent is extended or adjusted under 35 U.S.C. 154(b) by 230 days.

(21) Appl. No.: 17/641,827

(22) PCT Filed: Sep. 11, 2019

(86) PCT No.: PCT/CN2019/105368
§ 371 (c)(1),
(2) Date: Mar. 10, 2022

(87) PCT Pub. No.: WO2021/046752
PCT Pub. Date: Mar. 18, 2021

(65) Prior Publication Data
US 2024/0046415 A1     Feb. 8, 2024

(51) Int. Cl.
*G06T 5/00* (2024.01)
*A61B 1/00* (2006.01)
(Continued)

(52) U.S. Cl.
CPC .......... *G06T 5/00* (2013.01); *A61B 1/000095* (2022.02); *A61B 1/000096* (2022.02);
(Continued)

(58) Field of Classification Search
CPC . G06T 2207/10024; G06T 2207/10068; G06T 2207/20081; G06T 2207/20084;
(Continued)

(56) References Cited

U.S. PATENT DOCUMENTS

| | | |
|---|---|---|
| 6,132,368 A | 10/2000 | Cooper |
| 6,206,903 B1 | 3/2001 | Ramans |

(Continued)

FOREIGN PATENT DOCUMENTS

| | | |
|---|---|---|
| CN | 104217404 A | 12/2014 |
| CN | 105303532 A | 2/2016 |

(Continued)

OTHER PUBLICATIONS

J.-H. Wang, K.-E. Lin, S.-K. Lee and Y.-C. Lai, "Underwater Image Restoration via Machine Learning Transmission Map of Atmospheric Scattering Model," Oceans 2023—Limerick, Limerick, Ireland, 2023, pp. 1-4, doi: 10.1109/OCEANSLimerick52467.2023.10244677. (Year: 2023).*

(Continued)

*Primary Examiner* — Charles T Shedrick
(74) *Attorney, Agent, or Firm* — Carter, DeLuca & Farrell LLP

(57) ABSTRACT

A method for color restoration in images includes accessing an image of an object and processing the image based on an image processing operation to provide a processed image, where the image processing affects color of the object. The method further includes determining color adjustment parameters using a trained neural network, wherein an input to the trained neural network is based on the image and the processed image, restoring color in the processed image based on the color adjustment parameters to produce a color-restored image, and displaying the color-restored image on a display device.

18 Claims, 9 Drawing Sheets
(1 of 9 Drawing Sheet(s) Filed in Color)

(51) Int. Cl.
  *G06T 5/50* (2006.01)
  *G06T 5/90* (2024.01)
  *H04N 23/85* (2023.01)
  *H04N 23/86* (2023.01)

(52) U.S. Cl.
  CPC ............... *G06T 5/50* (2013.01); *G06T 5/90* (2024.01); *H04N 23/85* (2023.01); *H04N 23/86* (2023.01); *G06T 2207/10024* (2013.01); *G06T 2207/10068* (2013.01); *G06T 2207/20081* (2013.01); *G06T 2207/20084* (2013.01); *G06T 2207/20228* (2013.01)

(58) Field of Classification Search
  CPC ... G06T 2207/20228; G06T 5/60; G06T 7/90; G06T 5/73; G06N 3/045; G06N 3/08; H04N 1/60
  See application file for complete search history.

(56) References Cited

U.S. PATENT DOCUMENTS

| | | |
|---|---|---|
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |

(56) References Cited

U.S. PATENT DOCUMENTS

| | | |
|---|---|---|
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Piolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |

(56) References Cited

U.S. PATENT DOCUMENTS

| | | | |
|---|---|---|---|
| 10,595,946 B2 | 3/2020 | Nixon | |
| 10,881,469 B2 | 1/2021 | Robinson | |
| 10,881,473 B2 | 1/2021 | Itkowitz et al. | |
| 10,898,188 B2 | 1/2021 | Burbank | |
| 10,898,189 B2 | 1/2021 | McDonald, II | |
| 10,905,506 B2 | 2/2021 | Itkowitz et al. | |
| 10,912,544 B2 | 2/2021 | Brisson et al. | |
| 10,912,619 B2 | 2/2021 | Jarc et al. | |
| 10,918,387 B2 | 2/2021 | Duque et al. | |
| 10,918,449 B2 | 2/2021 | Solomon et al. | |
| 10,932,873 B2 | 3/2021 | Griffiths et al. | |
| 10,932,877 B2 | 3/2021 | Devengenzo et al. | |
| 10,939,969 B2 | 3/2021 | Swarup et al. | |
| 10,939,973 B2 | 3/2021 | DiMaio et al. | |
| 10,952,801 B2 | 3/2021 | Miller et al. | |
| 10,965,933 B2 | 3/2021 | Jarc | |
| 10,966,742 B2 | 4/2021 | Rosa et al. | |
| 10,973,517 B2 | 4/2021 | Wixey | |
| 10,973,519 B2 | 4/2021 | Weir et al. | |
| 10,984,567 B2 | 4/2021 | Itkowitz et al. | |
| 10,993,773 B2 | 5/2021 | Cooper et al. | |
| 10,993,775 B2 | 5/2021 | Cooper et al. | |
| 11,000,331 B2 | 5/2021 | Krom et al. | |
| 11,013,567 B2 | 5/2021 | Wu et al. | |
| 11,020,138 B2 | 6/2021 | Ragosta | |
| 11,020,191 B2 | 6/2021 | Diolaiti et al. | |
| 11,020,193 B2 | 6/2021 | Wixey et al. | |
| 11,026,755 B2 | 6/2021 | Weir et al. | |
| 11,026,759 B2 | 6/2021 | Donlon et al. | |
| 11,040,189 B2 | 6/2021 | Vaders et al. | |
| 11,045,077 B2 | 6/2021 | Stern et al. | |
| 11,045,274 B2 | 6/2021 | Dachs, II et al. | |
| 11,058,501 B2 | 7/2021 | Tokarchuk et al. | |
| 11,076,925 B2 | 8/2021 | DiMaio et al. | |
| 11,090,119 B2 | 8/2021 | Burbank | |
| 11,096,687 B2 | 8/2021 | Flanagan et al. | |
| 11,098,803 B2 | 8/2021 | Duque et al. | |
| 11,109,925 B2 | 9/2021 | Cooper et al. | |
| 11,116,578 B2 | 9/2021 | Hoffman et al. | |
| 11,129,683 B2 | 9/2021 | Steger et al. | |
| 11,135,029 B2 | 10/2021 | Suresh et al. | |
| 11,147,552 B2 | 10/2021 | Burbank et al. | |
| 11,147,640 B2 | 10/2021 | Jarc et al. | |
| 11,154,373 B2 | 10/2021 | Abbott et al. | |
| 11,154,374 B2 | 10/2021 | Hanuschik et al. | |
| 11,160,622 B2 | 11/2021 | Goldberg et al. | |
| 11,160,625 B2 | 11/2021 | Wixey et al. | |
| 11,161,243 B2 | 11/2021 | Rabindran et al. | |
| 11,166,758 B2 | 11/2021 | Mohr et al. | |
| 11,166,770 B2 | 11/2021 | DiMaio et al. | |
| 11,166,773 B2 | 11/2021 | Ragosta et al. | |
| 11,173,597 B2 | 11/2021 | Rabindran et al. | |
| 11,185,378 B2 | 11/2021 | Weir et al. | |
| 11,191,596 B2 | 12/2021 | Thompson et al. | |
| 11,197,729 B2 | 12/2021 | Thompson et al. | |
| 11,213,360 B2 | 1/2022 | Hourtash et al. | |
| 11,221,863 B2 | 1/2022 | Azizian et al. | |
| 11,234,700 B2 | 2/2022 | Ragosta et al. | |
| 11,241,274 B2 | 2/2022 | Vaders et al. | |
| 11,241,290 B2 | 2/2022 | Waterbury et al. | |
| 11,259,870 B2 | 3/2022 | DiMaio et al. | |
| 11,259,884 B2 | 3/2022 | Burbank | |
| 11,272,993 B2 | 3/2022 | Gomez et al. | |
| 11,272,994 B2 | 3/2022 | Saraliev et al. | |
| 11,291,442 B2 | 4/2022 | Wixey et al. | |
| 11,291,513 B2 | 4/2022 | Manzo et al. | |
| 12,100,124 B2 * | 9/2024 | Gubbi Lakshminarasimha ......... G06T 7/269 | |
| 2002/0181767 A1 * | 12/2002 | Deng ..................... G06V 10/56 382/165 | |
| 2010/0067823 A1 | 3/2010 | Kopf et al. | |
| 2011/0135200 A1 | 6/2011 | Chen et al. | |
| 2015/0339811 A1 | 11/2015 | Zhong et al. | |
| 2016/0005152 A1 | 1/2016 | Yang et al. | |
| 2019/0005603 A1 | 1/2019 | Chen et al. | |
| 2019/0287219 A1 * | 9/2019 | Guo ..................... H04N 23/76 |
| 2020/0242409 A1 * | 7/2020 | Wang ................... G06N 3/088 |
| 2021/0152735 A1 * | 5/2021 | Zhou .................... H04N 23/90 |

FOREIGN PATENT DOCUMENTS

| | | |
|---|---|---|
| CN | 105741248 A | 7/2016 |
| CN | 110136057 A | 8/2019 |
| IN | 106127702 A | 11/2016 |
| KR | 101976318 B1 | 5/2019 |

OTHER PUBLICATIONS

T. Zhang, H.-M. Hu and B. Li, "A Naturalness Preserved Fast Dehazing Algorithm Using HSV Color Space," in IEEE Access, vol. 6, pp. 10644-10649, 2018, doi: 10.1109/ACCESS.2018.2806372 (Year: 2018).*

"Image Dehazing Using Residual-Based Deep CNN," in IEEE Access, vol. 6, pp. 26831-26842, 2018 (Year: 2018).*

Extended European Search Report Dated May 9, 2023 for European Application No. 19944884.6 (20 pages).

Yoon et al., "Adaptive Defogging with Color Correction in the HSV Color Space for Consumer Surveillance System", IEEE Transactions on Consumer Electronics, Feb. 1, 2012, pp. 111-116, vol. 58, No. 1.

Bolun et al., "DehazeNet: An End-to-End System for Single Image Haze Removal", IEEE Transactions on Image Processing, Nov. 1, 2016, pp. 5187-5198, vol. 25, No. 11.

Shengdong et al., "Feed-Net: Fully End-to-End Dehazing", 2018 IEEE International Conference on Multimedia and Expo (ICME), IEEE, Jul. 23, 2018, pp. 1-6.

Bolkar et al., "Deep Smoke Removal from Minimally Invasive Surgery Videos", 2018 25th IEEE International Conference on Image Processing (ICIP), IEEE, Oct. 7, 2018, pp. 3403-3407.

International Search Report mailed Jun. 4, 2020 and Written Opinion completed May 28, 2020 corresponding to counterpart Int'l Patent Application PCT/CN2019/105368.

* cited by examiner

SYSTEMS AND METHODS FOR NEURAL-NETWORK BASED COLOR RESTORATION

CROSS-REFERENCE TO RELATED APPLICATION

The present application is a U.S. National Stage Application filed under 35 U.S.C. § 371(a) claiming the benefit of and priority to International Patent Application No. PCT/CN2019/105368, filed Sep. 11, 2019, the entire disclosure of which being incorporated by reference herein.

FIELD

The present disclosure relates to devices, systems, and methods for color restoration in images, and more particularly, to color restoration in dehazed images during surgical procedures.

BACKGROUND

Endoscopes are introduced through an incision or a natural body orifice to observe internal features of a body. Conventional endoscopes are used for visualization during endoscopic or laparoscopic surgical procedures. During electrosurgical procedures, it is possible for haze to be generated when the surgical instrument is used, for example, to treat tissue with electrosurgical energy during the surgery. Thus, the image acquired by the endoscope may include this haze. The haze may obscure features of the surgical site and delay the surgical procedure while surgeons wait for the haze to clear. Other procedures may experience similar issues where smoke is present during the capture of an image. Accordingly, there is interest in improving imaging technology.

SUMMARY

The present disclosure relates to devices, systems, and methods for color restoration in images. In accordance with aspects of the present disclosure, a method for color restoration in images includes accessing an image of an object and processing the image based on an image processing operation to provide a processed image, where the image processing affects color of the object. The method further includes determining color adjustment parameters using a trained neural network, where an input to the trained neural network is based on the image and the processed image, restoring color in the processed image based on the color adjustment parameters to produce a color-restored image, and displaying the color-restored image on a display device. The color restoration technique described herein can be applied to images resulting from image processing other than dehazing, as well.

In an aspect of the present disclosure, the image processing operation may include a dehazing operation to dehaze the image. The dehazing operation includes: determining a dark channel matrix of the image, estimating an atmospheric light component for the image, determining a transmission map based on the atmospheric light component and the dark channel matrix, and dehazing the image based on the transmission map to provide the processed image.

In another aspect of the present disclosure, the image may be an RGB image, and the processed image may be an RGB processed image.

In an aspect of the present disclosure, determining the color adjustment parameters may include: converting the RGB image to an HSV image, converting the RGB processed image to a HSV processed image, subtracting the HSV image from the HSV processed image to provide an HSV difference image, inputting the HSV difference image to the trained neural network, and obtaining an HSV adjustment image as an output of the trained neural network, the HSV adjustment image including the color adjustment parameters. Restoring color in the processed image may include adding a hue channel and a saturation channel of the HSV adjustment image to the HSV processed image to provide a HSV color-restored image, converting the HSV color-restored image to RGB to provide the color-restored image.

In yet another aspect of the present disclosure, the method may further include training the neural network. The training includes: accessing a RGB haze-free image dataset having haze-free images, accessing a RGB haze dataset having images of haze on a dark background, combining the RGB haze-free image dataset with the RGB haze dataset to provide a RGB hazy image data set, dehazing images in the RGB hazy image dataset to provide a RGB dehazed image dataset, converting the RGB dehazed image dataset, the RGB hazy image dataset, and the RGB haze-free image dataset from RGB images to HSV images, to provide a HSV dehazed image dataset, a HSV hazy image dataset, and an HSV haze-free image dataset, respectively, determining a difference between images in the HSV dehazed image dataset and corresponding images in the HSV hazy image dataset to provide an HSV difference image dataset, and providing the HSV difference image dataset as a training input to the neural network.

In a further aspect of the present disclosure, training the neural network may further include decreasing a loss function. The loss function may be based on at least a portion of the HSV difference image dataset.

In an aspect of the present disclosure, the loss function is further based on a ground truth, the ground truth being based on a difference between an image of the HSV haze-free image dataset and a corresponding image of the HSV hazy image dataset.

In a further aspect of the present disclosure, the method may further include combining the RGB haze-free image dataset with the RGB haze dataset by determining a weighted combination using the formula: image in the RGB haze dataset*coeff+image in the RGB haze-free image dataset*(1−coeff). The coeff is a value between 0 and 1.

In yet another aspect of the present disclosure, the neural network may include a convolutional neural network and/or a fully connected neural network.

In a further aspect of the present disclosure, the convolutional neural network may include: a first convolution layer having outputs. The convolutional neural network further includes a first rectified linear unit configured to receive the outputs of the first convolution layer, a middle convolution layer configured to receive outputs of the first rectified linear unit, a middle rectified linear unit configured to receive outputs of the middle convolution layer, a last convolution layer configured to receive outputs of the middle rectified linear unit, and a last rectified linear unit configured to receive outputs of the last convolution layer. The middle convolution layer and the middle rectified linear unit are configured to iterate for a number of iterations.

In accordance with aspects of the present disclosure, a system for color restoration in images includes a display device, a processor, and a memory storing instructions. The instructions, when executed by the processor, cause the system to: access an image of an object, process the image based on an image processing operation to provide a processed image, wherein the image processing affects color of the object, and determine color adjustment parameters using a trained neural network. An input to the trained neural network is based on the image and the processed image. The instructions further cause the system to: restore color in the processed image based on the color adjustment parameters to produce a color-restored image and display the color-restored image on the display device.

In yet a further aspect of the present disclosure, the image processing operation may include a dehazing operation to dehaze the image. The instructions, when performing the dehazing operation further cause the system to: determine a dark channel matrix of the image, estimate an atmospheric light component for the image, determine a transmission map based on the atmospheric light component and the dark channel matrix, and dehaze the image based on the transmission map to provide the processed image.

In yet another aspect of the present disclosure, the image may be an RGB image, and the processed image may be an RGB processed image.

In a further aspect of the present disclosure, the instructions, when determining the color adjustment parameters may further cause the system to: convert the RGB image to an HSV image, convert the RGB processed image to a HSV processed image, subtract the HSV image from the HSV processed image to provide an HSV difference image, input the HSV difference image to the trained neural network, and obtain an HSV adjustment image as an output of the trained neural network, the HSV adjustment image including color adjustment parameters. Restoring color in the processed image includes: adding a hue channel and a saturation channel of the HSV adjustment image to the HSV processed image, to provide an HSV color-restored image and convert the HSV color-restored image to RGB to provide the color-restored image.

In yet a further aspect of the present disclosure, the instructions when training the neural network may further cause the system to: access a RGB haze-free image dataset having haze-free images, access an RGB haze dataset having images of haze on a dark background, combine the RGB haze-free image dataset with the RGB haze dataset to provide a RGB hazy image data set, dehaze images in the RGB hazy image dataset to provide a RGB dehazed image dataset, convert the RGB dehazed image dataset, the RGB hazy image dataset, and the RGB haze-free image dataset from RGB images to HSV images, to provide a HSV dehazed image dataset, a HSV hazy image dataset, and a HSV haze-free image dataset respectively, determine a difference between images in the HSV dehazed image dataset and corresponding images in the HSV hazy image dataset to provide an HSV difference image dataset, and provide the HSV difference image dataset as a training input to the neural network.

In yet another aspect of the present disclosure, training the neural network may further include decreasing a loss function, the loss function being based on at least a portion of the HSV difference image dataset.

In a further aspect of the present disclosure, the loss function may be further based on a ground truth, the ground truth being based on a difference between an image of the HSV haze-free image dataset and a corresponding image of the HSV hazy image dataset.

In an aspect of the present disclosure, combining the RGB haze-free image dataset with the RGB haze dataset includes determining a weighted combination using the formula: image in the RGB haze dataset*coeff+image in the RGB haze-free image dataset*(1−coeff). The coeff is a value between 0 and 1.

In another aspect of the present disclosure, the neural network may include a convolutional neural network and/or a fully connected neural network.

In a further aspect of the present disclosure, the convolutional neural network may include: a first convolution layer having outputs, a first rectified linear unit configured to receive outputs of the first convolution layer, a middle convolution layer configured to receive outputs of the first rectified linear unit, a middle rectified linear unit configured to receive outputs of the middle convolution layer, a last convolution layer configured to receive outputs of the middle rectified linear unit, and a last rectified linear unit configured to receive outputs of the last convolution layer. The middle convolution layer and the middle rectified linear unit may loop twenty times.

Further details and aspects of various embodiments of the present disclosure are described in more detail below with reference to the appended figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the present disclosure are described herein with reference to the accompanying drawings, wherein.

Figure 1:
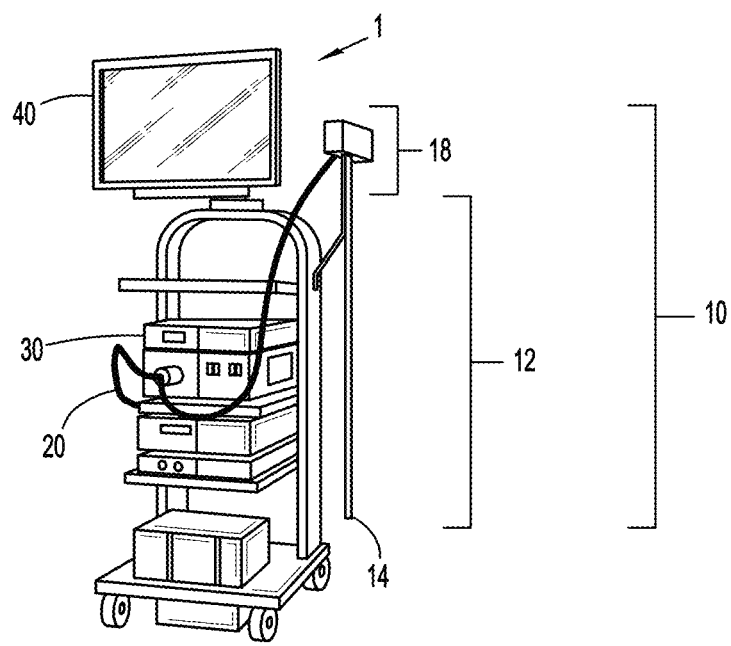
FIG. 1 is a diagram of an exemplary visualization or endoscope system in accordance with the present disclosure.

Further details and aspects of exemplary embodiments of the disclosure are described in more detail below with reference to the appended figures. Any of the above aspects and embodiments of the disclosure may be combined without departing from the scope of the disclosure.

DETAILED DESCRIPTION OF EMBODIMENTS

Embodiments of the presently disclosed devices, systems, and methods of treatment are described in detail with reference to the drawings, in which like reference numerals designate identical or corresponding elements in each of the several views. As used herein, the term "distal" refers to that portion of a structure that is farther from a user, while the term "proximal" refers to that portion of a structure that is closer to the user. The term "clinician" refers to a doctor, nurse, or other care provider and may include support personnel.

The present disclosure is applicable where images of a surgical site are captured. Endoscope systems are provided as an example, but it will be understood that such description is exemplary and does not limit the scope and applicability of the present disclosure to other systems and procedures.

Figure 2:
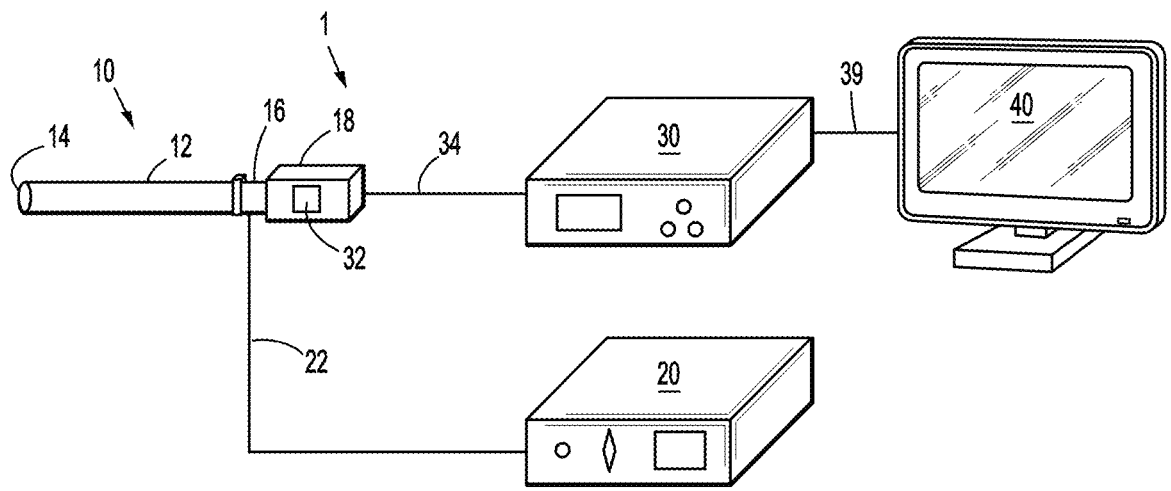
FIG. 2 is a schematic configuration of the visualization or endoscope system of FIG. 1.
Figure 3:
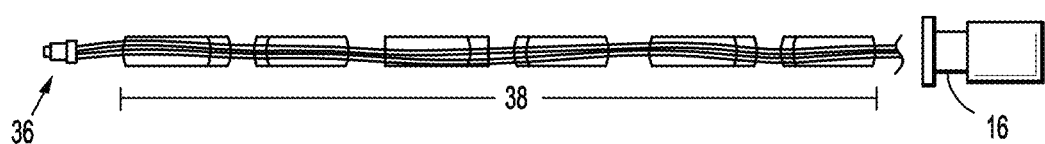
FIG. 3 is a diagram illustrating another schematic configuration of an optical system of the system of FIG. 1.

Referring initially to FIGS. 1-3, an endoscope system 1, in accordance with aspects of the present disclosure, includes an endoscope 10, a light source 20, a video system 30, and a display device 40. The light source 20, such as an LED/Xenon light source, is connected to the endoscope 10 via a fiber guide 22 that is operatively coupled to the light source 20 and to an endocoupler 16 disposed on, or adjacent to, a handle 18 of the endoscope 10. The fiber guide 22 includes, for example, fiber optic cable which extends through the elongated body 12 of the endoscope 10 and terminates at a distal end 14 of the endoscope 10. Accordingly, light is transmitted from the light source 20, through the fiber guide 22, and emitted out the distal end 14 of the endoscope 10 toward a targeted internal feature, such as tissue or an organ, of a body of a patient. As the light transmission pathway in such a configuration may be relatively long (for example, the fiber guide 22 may be about 1.0 m to about 1.5 m in length), only about 15% (or less) of the light flux emitted from the light source 20 may be outputted from the distal end 14 of the endoscope 10.

With reference to FIG. 2 and FIG. 3, the video system 30 is operatively connected to an image sensor 32 mounted to, or disposed within, the handle 18 of the endoscope 10 via a data cable 34. An objective lens 36 is disposed at the distal end 14 of the elongated body 12 of the endoscope 10 and a series of spaced-apart, relay lenses 38, such as rod lenses, are positioned along the length of the elongated body 12 between the objective lens 36 and the image sensor 32. Images captured by the objective lens 36 are forwarded through the elongated body 12 of the endoscope 10 via the relay lenses 38 to the image sensor 32, which are then communicated to the video system 30 for processing and output to the display device 40 via cable 39. The image sensor 32 is located within, or mounted to, the handle 18 of the endoscope 10, which can be up to about 30 cm away from the distal end 14 of the endoscope 10.

The following description will now refer various flow and block diagrams, including various blocks described in an ordered sequence. However, those skilled in the art will appreciate that one or more blocks of the flow or block diagrams may be performed in a different order, repeated, and/or omitted without departing from the scope of the present disclosure. The below description of the flow diagram refers to various actions or tasks performed by one or more video system 30, but those skilled in the art will appreciate that the video system 30 is exemplary. In various embodiments, the disclosed operations can be performed by another component, device, or system. In various embodiments, the video system 30 or other component/device performs the actions or tasks via one or more software applications executing on a processor. In various embodiments, at least some of the operations can be implemented by firmware, programmable logic devices, and/or hardware circuitry. Other implementations are contemplated to be within the scope of the present disclosure.

Figure 4:
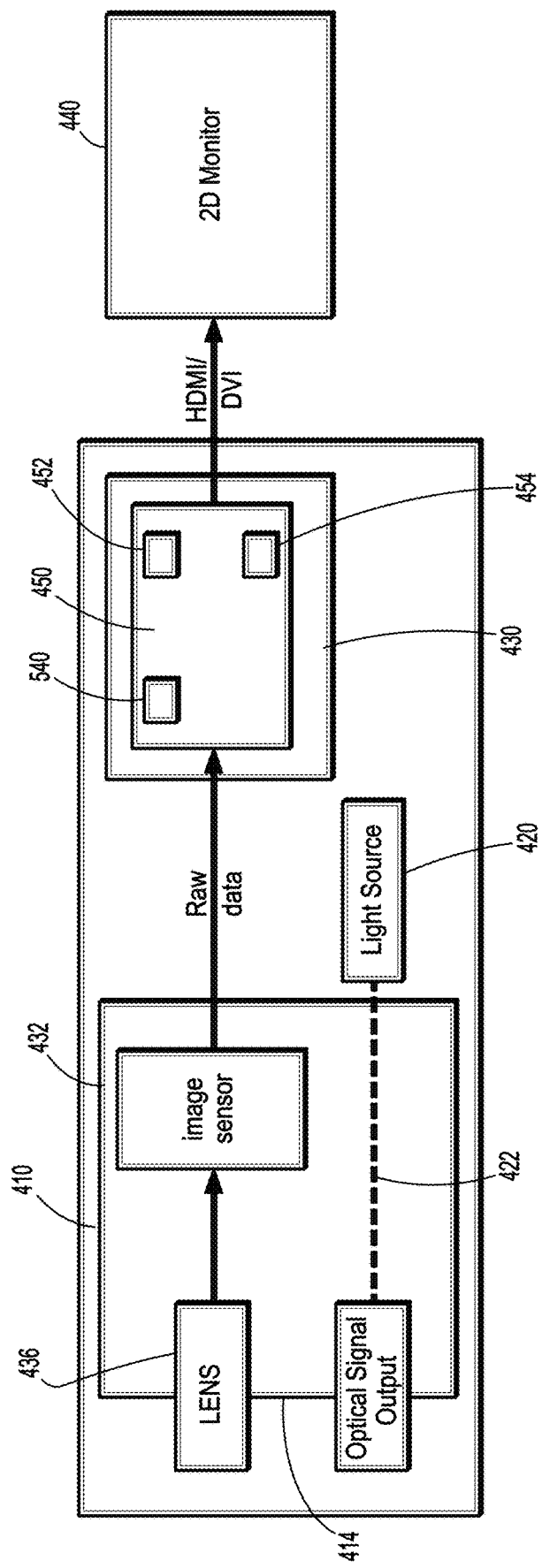
FIG. 4 is a block diagram of the visualization or endoscope system in accordance with an embodiment of the present disclosure.

Referring to FIG. 4, there is shown a block diagram of a system, which may be the endoscope system of FIG. 1 or may be a different type of system (e.g., visualization system, etc.). The system, in accordance with aspects of the present disclosure, includes an imaging device 410, a light source 420, a video system 430, and a display device 440. The light source 420 is configured to provide light to a surgical site through the imaging device 410 via the fiber guide 422. The distal end 414 of the imaging device 410 includes an objective lens 436 for capturing the image at the surgical site. The objective lens 436 forwards the image to the image sensor 432. The image is then communicated to the video system 430 for processing. The video system 430 includes an imaging device controller 450 for controlling the endoscope and processing the images. The imaging device controller 450 includes processor 452 connected to a computer-readable storage medium or a memory 454, which may be a volatile type memory, such as RAM, or a non-volatile type memory, such as flash media, disk media, or other types of memory. In various embodiments, the processor 452 may be another type of processor such as, without limitation, a digital signal processor, a microprocessor, an ASIC, a graphics processing unit (GPU), field-programmable gate array (FPGA), or a central processing unit (CPU).

In various embodiments, the memory 454 can be random access memory, read-only memory, magnetic disk memory, solid-state memory, optical disc memory, and/or another type of memory. In various embodiments, the memory 454 can be separate from the imaging device controller 450 and can communicate with the processor 452 through communication buses of a circuit board and/or through communication cables such as serial ATA cables or other types of cables. The memory 454 includes computer-readable instructions that are executable by the processor 452 to operate the imaging device controller 450. In various embodiments, the imaging device controller 450 may include a network interface 540 to communicate with other computers or a server.

In the systems of FIGS. 1-4, it is possible for haze to be generated when an electrosurgical instrument is used, for example, to treat tissue with electrosurgical energy during the surgery. Thus, the acquired image may include this haze. The haze may obscure features of the surgical site and delay the surgical procedure while surgeons wait for the haze to clear. The following will describe an operation that dehazes an image while also preserving color of the surgical site.

Figure 5:
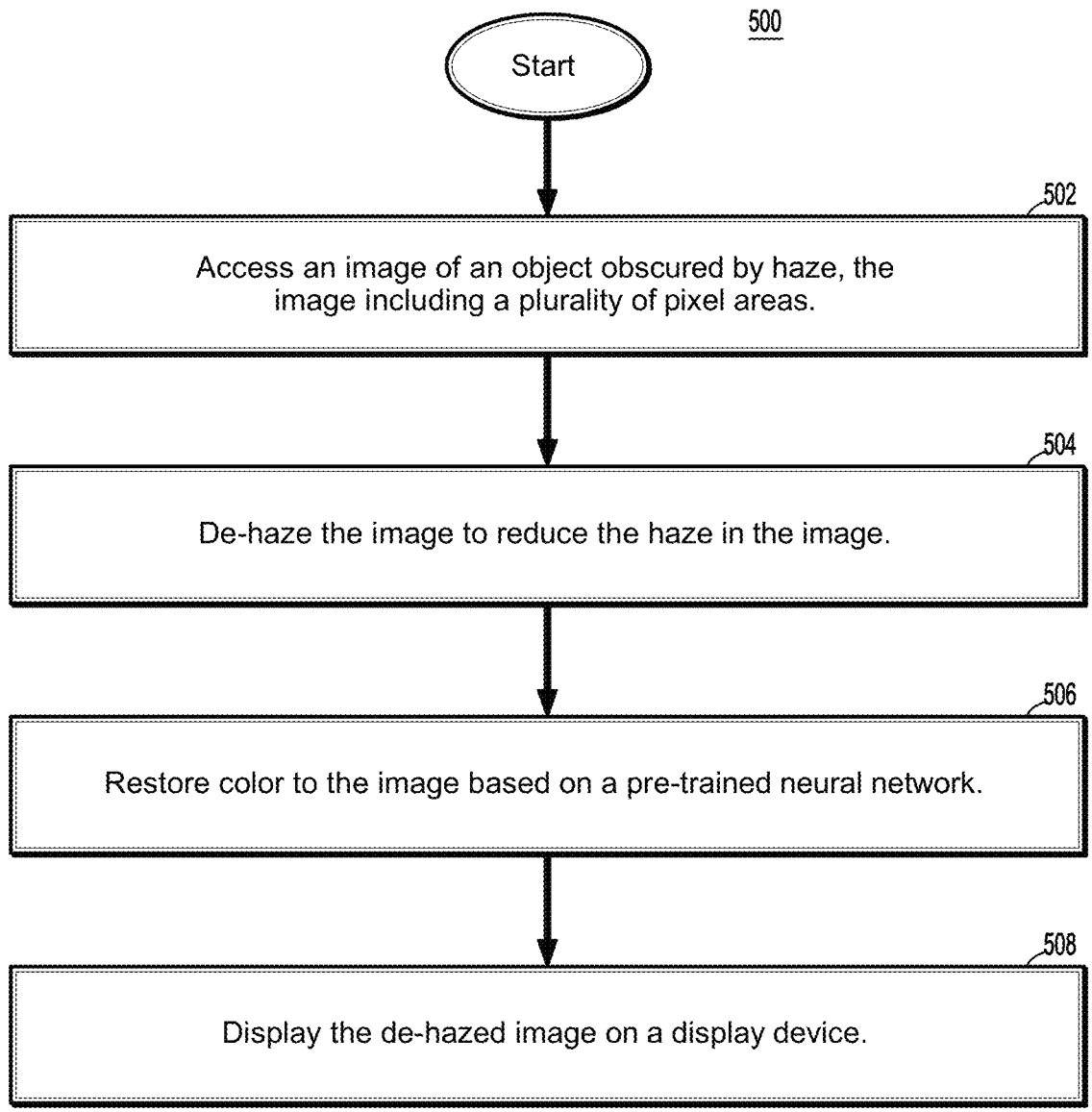
FIG. 5 is a flowchart of a method for color restoration in accordance with the disclosure.

Referring now to FIG. 5, there is shown an operation for dehazing and for color restoration in images. In various embodiments, the operation of FIG. 5 can be performed by an endoscope system 1 described above herein. In various embodiments, the operation of FIG. 5 can be performed by another type of system and/or during another type of procedure. The following description will refer to an endoscope system, but it will be understood that such description is exemplary and does not limit the scope and applicability of the present disclosure to other systems and procedures. The following description will refer to an RGB (Red, Green, Blue) image or RGB color model, but it will be understood that such description is exemplary and does not limit the scope and applicability of the present disclosure to other types of images or color models (for example, CMYK (Cyan, Magenta, Yellow, Key), CIELAB, or CIEXYZ). The image sensor 32 may capture raw data. The format of the raw data may be RGGB, RGBG, GRGB, or BGGR. The video system 30 may convert the raw data to RGB using a demosaicing algorithm. A demosaicing algorithm is a digital image process used to reconstruct a full color image from the incomplete color samples output from an image sensor overlaid with a color filter array (CFA). It is also known as CFA interpolation or color reconstruction. The RGB image may be further converted by the video system 30 to another color model, such as CMYK, CIELAB, or CIEXYZ.

Initially, at step 502, the operation accesses an image of a surgical site. The image can be captured via the objective lens 36 and forwarded to the image sensor 32 of endoscope system 1. The term "image" as used herein may include still images or moving images (for example, video). In various embodiments, the captured image is communicated to the video system 30 for processing. For example, during an endoscopic procedure a surgeon may cut tissue with an electrosurgical instrument. During this cutting, haze such as smoke or fog may be generated. When the image is captured, it may include the haze. Haze is generally a turbid medium (such as particles, water droplets) in the atmosphere, which can be an enclosed atmosphere in the body cavity of a patient. The irradiance received by the objective lens 36 from the scene point is attenuated by the line of sight. This incoming light is mixed with ambient light (air-light) reflected into the line of sight by atmospheric particles such as smoke. This haze degrades the image, making it lose contrast and color fidelity.

At step 504, the operation dehazes the image to reduce the haze in the image. A dehazing operation will be described in more detail in connection with FIGS. 6 and 7. At step 506, the operation restores color to the image based on a pretrained neural network. The neural network will be described in more detail in connection with FIGS. 8 and 11, and application of the neural network to restore color will be described in more detail in connection with FIGS. 9 and 10. At step 508, the image resulting from the dehazing and color restoration operations is displayed on a display device. As described above herein, the color restoration technique described herein can be applied to images resulting from image processing other than dehazing operations. Although dehazing is used herein as an example, it is contemplated that color restoration for other types of image processing is within the scope of the present disclosure.

Figure 6:
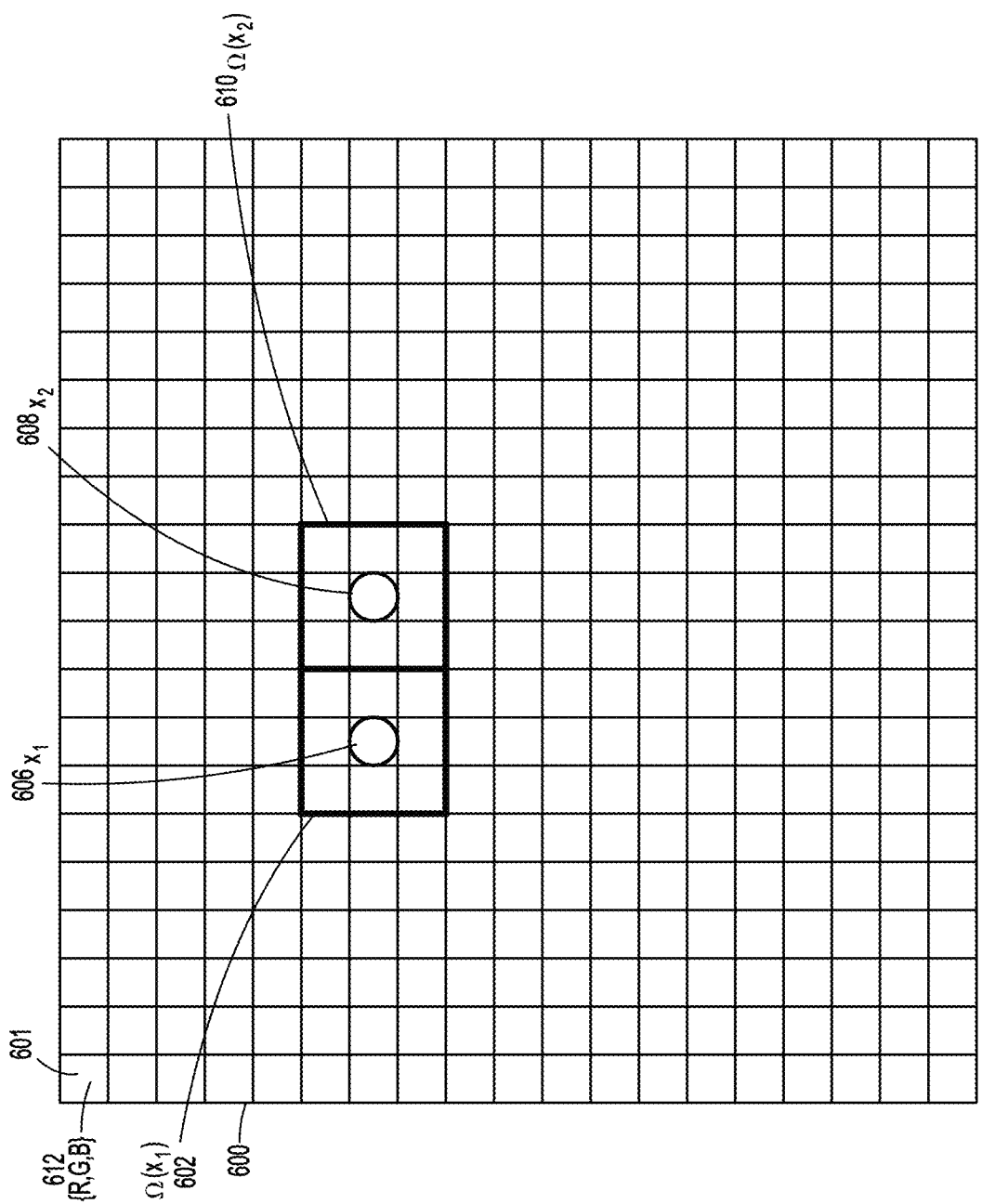
FIG. 6 is an exemplary input image including an area of pixels in accordance with the present disclosure.

Referring now to FIG. 6, there is shown an exemplary pixel representation of an image accessed in step 502. In various embodiments, the captured image may or may not have been processed during the capture process or after the capture process. In various embodiments, an image 600 includes a number of pixels, and the dimensions of the image 600 are often represented as the amount of pixels in an X by Y format, such as 500×500 pixels, for example. In accordance with aspects of the present disclosure, and as explained in more detail later herein, each pixel of the image 600 may be processed based on a pixel area 602, 610, centered at that pixel, which will also be referred to herein as a patch. In various embodiments, each patch/pixel area of the image can have the same size. In various embodiments, different pixel areas or patches can have different sizes. Each pixel area or patch can be denoted as $\Omega(x)$, which is a pixel area/patch having a particular pixel "x" as its center pixel. In the illustrative example of FIG. 6, the pixel area 602 has a size of 3×3 pixels and is centered at a particular pixel $x_1$ 606, and the pixel area 610 has a size 3×3 pixels and is centered at a particular pixel $x_2$ 608. If an image has 18 by 18 pixels, a patch size may be 3×3 pixels. The illustrated image size and patch size are exemplary and other image sizes and patch sizes are contemplated to be within the scope of the present disclosure. For cases where the center pixel of the patch is at or near the edge of the image, only the part of the patch in the image is used.

With continuing reference to FIG. 6, each pixel 601 in an image 600 may have combinations of color components 612, such as red, green, and blue, which are also referred to herein as color channels. $I^c(y)$ is used herein to denote the intensity value of a color component c of a particular pixel y in the image 600. For a pixel 601, each of the color components 612 has an intensity value representing the brightness intensity of that color component. For example, for a 24 bit RGB image, each of the color components 612 has 8 bits, which corresponds to each color component having 256 possible intensity values.

In accordance with aspects of the present disclosure, the image 600 can include haze, and the video system 30 (FIG. 2) can dehaze the image 600 to reduce the haze in the image. An exemplary dehazing operation is described in Kaiming He et al., "Single Image Haze Removal Using Dark Channel Prior," IEEE Transactions On Pattern Analysis And Machine Intelligence, Vol. 33, No. 12, December 2011, the entire contents of which are hereby incorporated by reference herein. Such dehazing operation will be described below herein, but it is contemplated that such dehazing operation is exemplary and other dehazing techniques are contemplated to be within the scope of the present disclosure. In various embodiments, the dehazing may include determining a dark channel matrix of the image, estimating an atmospheric light component for the image, and determining a transmission map based on the atmospheric light component and the dark channel matrix, which will be explained below and also later in connection with FIG. 7.

With continuing reference to FIG. 6, in various embodiments, the dehazing operation may be based on what is referred to herein as a "dark channel matrix." In various embodiments, the video system 30 (FIG. 2) can determine a dark channel matrix for the image 600. As used herein, the phrase "dark channel" of a pixel refers to the lowest color component intensity value among all pixels of the patch $\Omega(x)$ 602 centered at are particular pixel x. The term "dark channel matrix" of an image, as used herein, refers to a matrix of the dark channel of every pixel of the image. The dark channel of a pixel x will be denoted as I_DARK(x). In various embodiments, the video system 30 calculates the dark channel of a pixel as follows:

$$I\_DARK(x) = \min_{(x)}(\min(I^c(y))), \text{ for all } c \in \{r,g,b\} y \in \Omega$$

where y denotes a pixel of the patch $\Omega(x)$, c denotes a color component, and $I^c(y)$ denotes the intensity value of the color component c of pixel y. Thus, the dark channel of a pixel is the outcome of two minimum operations across two variables c and y, which together determine the lowest color component intensity value among all pixels of a patch. In various embodiments, the video system 30 can calculate the dark channel of a pixel x by acquiring the lowest color component intensity value for every pixel in the patch $\Omega(x)$ and then finding the minimum value among all of those values.

For example, with reference to FIG. 6, the image 600 may have a height and width of 18×18 pixels, and the pixel area (patch) size may be 3×3 pixels. For example, a 3×3 pixel area $\Omega(x_1)$ 602 centered at $x_1$ 606 may have the following intensities for the R, G, and B components for each of the 9 pixels in the patch:

$$\begin{bmatrix} 1,3,6 & 2,0,1 & 5,3,4 \\ 2,4,3 & 6,7,4 & 7,6,9 \\ 1,3,2 & 5,8,9 & 9,11,25 \end{bmatrix}$$

In this example, for the top left pixel in the pixel area Ω(x₁) 602, the R component may have an intensity of 1, the G component may have an intensity of 3, and the B component may have an intensity of 6. In this example, the R component has the minimum intensity value (a value of 1) of the RGB components for that pixel.

The minimum color component intensity value of each the pixels would be determined. In the above example, for the 3×3 pixel area Ω(x₁) 602 centered at x₁ the minimum color component intensity value for each of the pixels in the pixel area Ω(x₁) 602 are:

$$\begin{bmatrix} 1 & 0 & 3 \\ 2 & 4 & 6 \\ 1 & 5 & 9 \end{bmatrix}$$

Thus, the dark channel of the pixel would have an intensity value of 0 for this exemplary 3×3 pixel area Ω(x₁) 602 centered at x₁. In this manner, the dark channel can be determined for each pixel of the image 600, and the dark channel for all pixels form the dark channel matrix for the image 600.

In various embodiments, the dehazing operation involves estimating what is referred to herein as an "atmospheric light component" for the image. The estimated atmospheric light component for the image will be denoted herein as A. In various embodiments, the dehazing operation may estimate the atmospheric light component from the most haze-opaque pixel in the image. In various embodiments, the atmospheric light component A can be determined based on finding the lowest color component intensity value for each pixel in the image 600, such as min(I^R(x), I^G(x), I^B(x)) for every pixel "x" in the image 600, and then finding the maximum among these lowest color component intensity values.

In various embodiments, the dehazing operation determines what is referred to herein as a transmission map T. The transmission map includes a transmission component T(x) for each pixel x. The transmission map value T(x) for a pixel x is determined based on the dark channel of pixel x and the atmospheric light component A as follows:

$$T(x) = 1 - \omega * \frac{I\_DARK(X)}{A},$$

where ω is a parameter having a value between 0 and 1, such as 0.85. In practice, even in clear images, there are some particles. Thus, some haze exists when distant objects are observed. The presence of haze is a cue to human perception of depth. If all haze is removed, the perception of depth may be lost. Therefore, to retain some haze, the parameter ω (0<ω<=1) is introduced. In various embodiments, the value of ω can vary based on the particular application. Thus, the transmission map for a pixel is equal to 1 minus ω times the dark channel of the pixel (I–DARK(x)) divided by the atmospheric light component value for the image 600. The transmission map is used in the dehazing process described in Kaiming He et al., "Single Image Haze Removal Using Dark Channel Prior," IEEE Transactions On Pattern Analysis And Machine Intelligence, Vol. 33, No. 12, December 2011, the entire contents of which were previously incorporated by reference herein. The dehazing operation described above in connection with FIG. 6 is exemplary, and other dehazing techniques are contemplated to be within the scope of the present disclosure. Additionally, even though the present disclosure uses dehazing as an example of image processing, other types of image processing are applicable.

Figure 7:
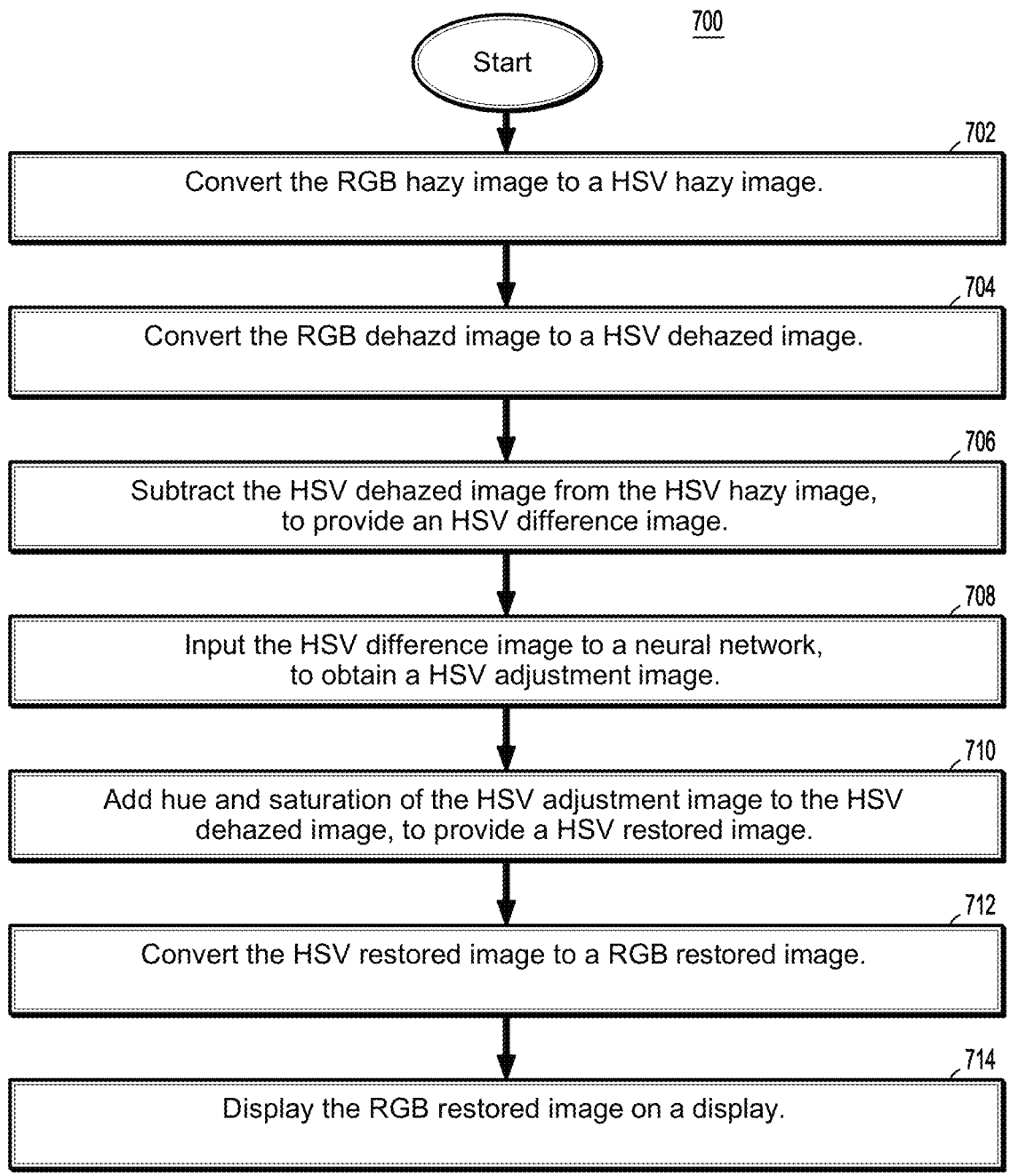
FIG. 7 is a flowchart of a method for restoring color in accordance with the disclosure.

With reference to FIG. 7, a color restoration operation is described. The illustrated operation assumes that the original image is an RGB image. The operation attempts to restore the original color of a processed image. In the process of restoring color, the operation converts an RGB image to an HSV image, which persons skilled in the art will understand refers to a hue-saturation-value color model. Generally, hue may be understood to specify a particular ideal color. Saturation may be understood to vary the "fullness" of that color such that zero saturation results in white and increasing saturation approach the ideal color. The "value" parameter may be understood to specify a brightness, such that zero brightness results in black and increasing value approaches the idea color.

Initially, at step 702, the video system 30 converts the RGB hazy image 600 to an HSV hazy image denoted as I_HSV. Next, at step 704, the video system 30 converts the image dehazed in step 504 to an HSV dehazed image denoted as J_HSV.

Next, at step 706, the video system 30 subtracts the HSV hazy image I_HSV from the HSV dehazed image J_HSV to provide an HSV difference image D_HSV as follows:

D_HSV=J_HSV–I_HSV

The HSV dehazed image J_HSV is generally darker than the original HSV hazy image I_HSV because haze generally appears lighter. In HSV color space, darker corresponds to a higher saturation value, and brighter corresponds to a lower saturation value. Accordingly, the saturation values in the HSV difference image J_HSV will generally be positive values. However, for other types of image processing, the saturation values in the difference image may be negative. Additionally, the hue values of the difference image may be positive or negative depending on the direction of color change and/or the type of image processing. In general, the HSV difference image D_HSV reflects changes in hue and saturation related to the image processing, which in the above examples relate to the dehazing image processing.

Next, at step 708, the video system 30 inputs the HSV difference image D_HSV to a trained neural network and outputs an HSV adjustment image F_HSV. Aspects of the neural network will be described in connection with FIGS. 9 and 11. In accordance with aspects of the present disclosure, the trained neural network converts the HSV difference image D_HSV to hue and saturation adjustment values that can be used to adjust the color of the dehazed image J_HSV. Thus, the HSV adjustment image F_HSV includes the hue and saturation adjustment values.

Next, at step 710, the video system 30 adds the hue and saturation adjustment values of the adjustment image F_HSV to the HSV dehazed image J_HSV and outputs an HSV restored image R_HSV, as follows:

Hue of R_HSV=Hue of J_HSV+Hue of F_HSV

Saturation of R_HSV=Saturation of J_HSV+Saturation of F_HSV

Value of R_HSV=Value of J_HSV

Next, at step 712, the video system 30 converts the HSV restored image R_HSV to an RGB restored image R_RGB.

Finally, at step 714, the video system 30 may display the RGB restored image on a display. In various embodiments, the video system 30 may communicate the resultant RGB dehazed and color-restored image on the display device 40 and/or save it to a memory or external storage device for later recall or further processing. Although the operation of FIG. 7 is described with respect to an RGB image, it will be understood that the disclosed operation can be applied to other color spaces as well. Additionally, the color restoration operation of FIG. 7 can apply to image processing other than dehazing image processing, and can operate to restore color in images resulting from such other image processing.

Figure 8:
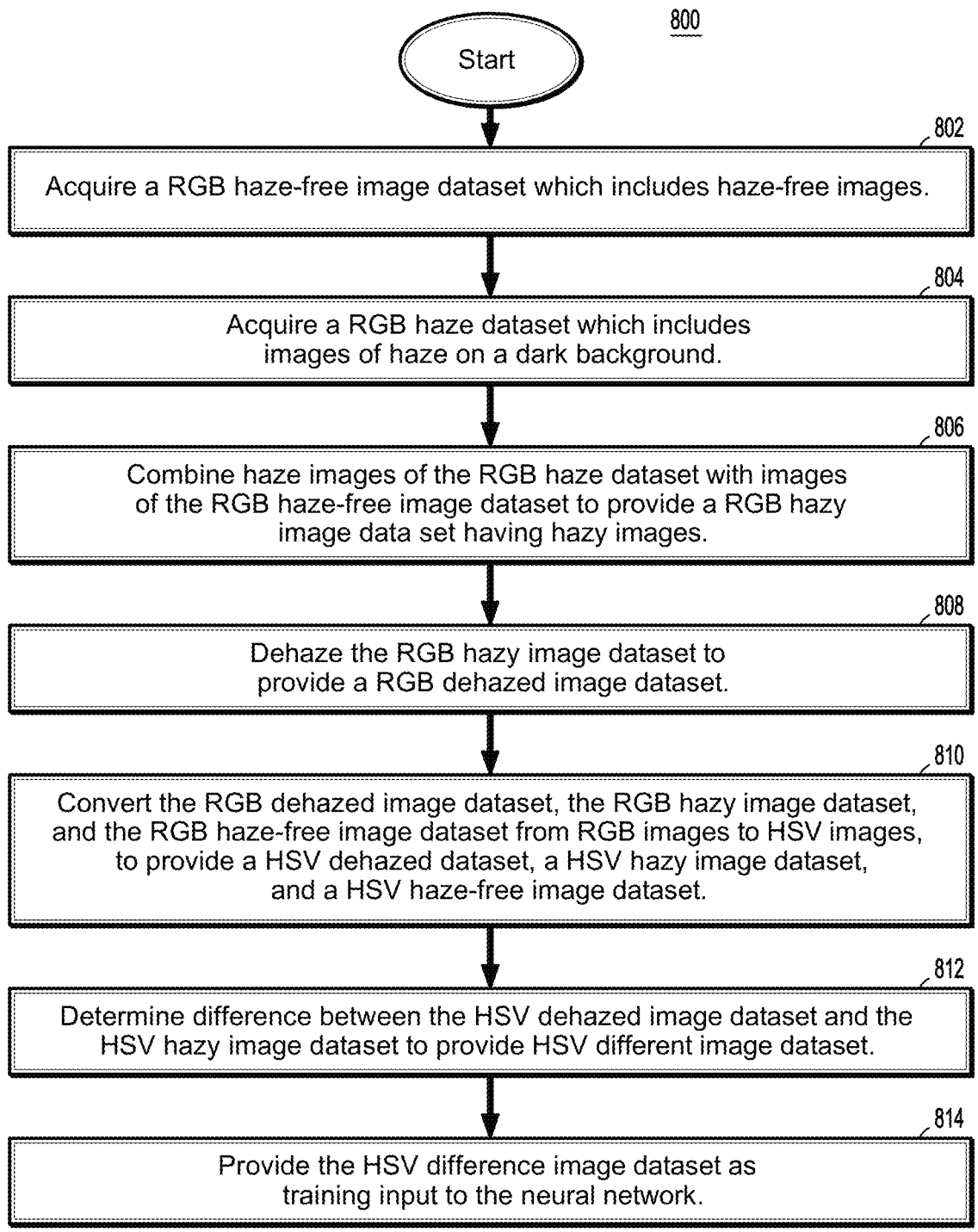
FIG. 8 is a flowchart of a method for performing training of a neural network in accordance with the disclosure.

With reference to FIG. 8, a method for generating training data for training the neural network, in accordance with aspects of the present disclosure, is shown. It is contemplated that the training may be performed on a system separate from the systems of FIGS. 1-4, including, for example, on GPU servers, simulation, etc., and the trained network would then be deployed in the video system 30.

Initially, at step 802, the training operation acquires an RGB haze-free image dataset C_S which includes haze-free images. In various embodiments, the image set may include at least thousands of clean, haze-free images taken with a laparoscope. Next at step 804, training operation acquires an RGB haze dataset N_S which includes images of haze on a dark background. In the RGB space, a black background has zero values for the R, G, and B color components.

Next, at step 806, the training operation may combine the haze of the RGB haze dataset N_S with the images of the RGB haze-free image dataset C_S to provide an RGB hazy image data set I_S of hazy images. In various embodiments, the images can be combined in various ways. For example, the combined image may be a weighted sum of the individual images, such as:

image in I_S=(image in N_S)*coef+(image in C_S)* (1−coef), where coef is a value between 0 to 1.

Next, at step 808, the training operation dehazes the hazy images of the RGB hazy image dataset I_S to provide dehazed images in an RGB dehazed images dataset J_S. It is contemplated that various dehazing algorithms may be used, including the dehazing operation described above in connection with FIG. 6. Next at step 810, the training operation converts the RGB dehazed image dataset J_S, the RGB hazy image dataset I_S, and the RGB haze-free image dataset C_S from RGB images to HSV images, to provide an HSV dehazed image dataset J_S_HSV, an HSV hazy image dataset I_S_HSV, and an HSV haze-free image dataset C_S_HSV.

Next, at step 812, the training operation determines a difference between the dehazed images of the HSV dehazed image dataset J_S_HSV and the corresponding hazy images of the HSV hazy image dataset I_S_HSV to provide difference images of an HSV difference image dataset D_S_HSV. Finally, at step 814, the training operation provides the difference images of the HSV difference image dataset D_S_HSV as training input data to the neural network. As described below, the outputs of the neural network are hue and saturation adjustment values that should be added to the HSV dehazed images to restore the colors.

In various embodiments, the training operation provides a ground truth of the training as a difference between the HSV haze-free image dataset C_S_HSV and the HSV hazy image dataset I_S_HSV. In various embodiments, the loss function may include a mean square error, and the error of the neural network's prediction for the hue and saturation adjustment values can be expressed at a high level as:

(image of J_S_HSV−image of I_S_HSV+neural network output)−(image of C_S_HSV−image of I_S_HSV).

Persons skilled in the art will recognize techniques for minimizing a loss function to improve the accuracy of a neural network's predictions. In various embodiments, the error of the neural network's prediction for the hue and saturation adjustment values can be expressed as:

neural network output−(image of C_S_HSV−image of J_S_HSV), such that the ground truth for the training can be based on a difference between the HSV haze-free image dataset C_S_HSV and the HSV dehazed image dataset J_S_HSV. A particular neural network structure will be described in connection with FIG. 11.

Figure 9:
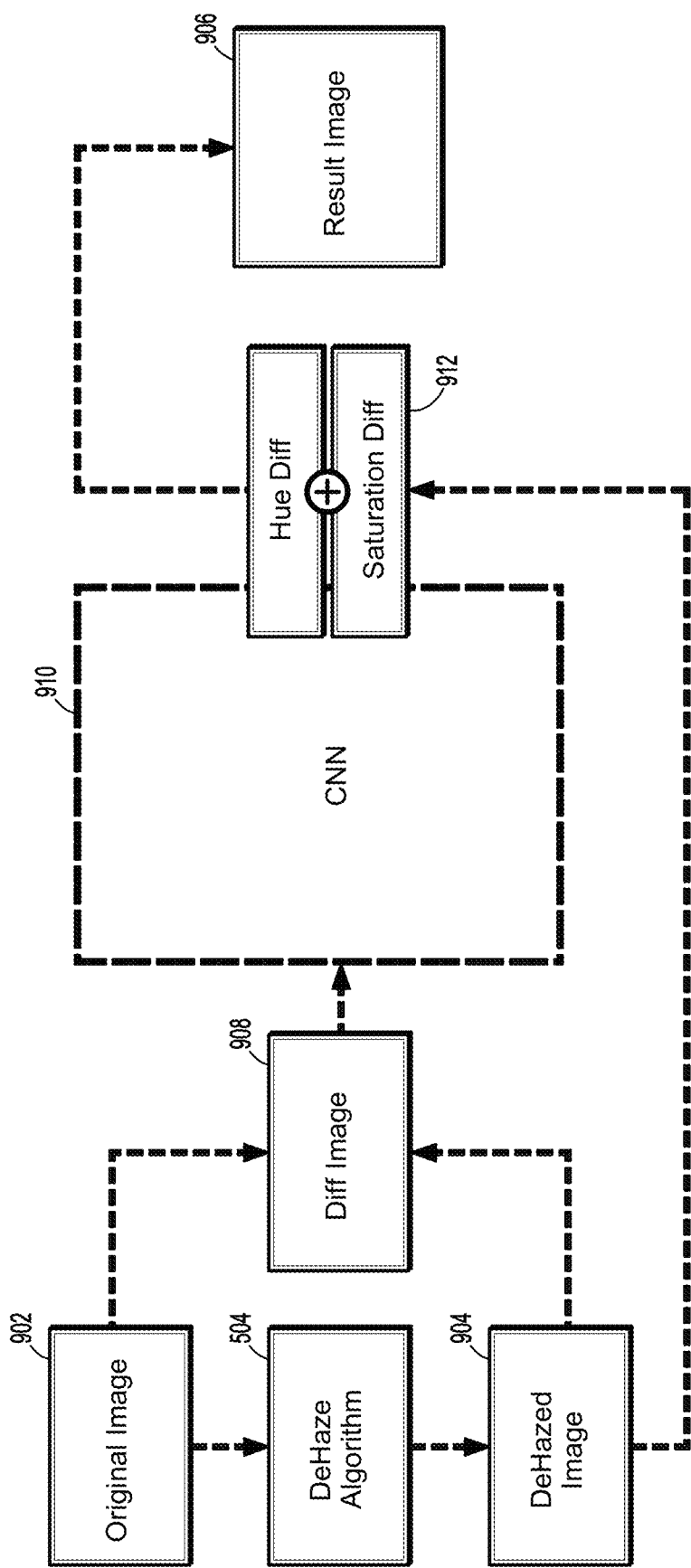
FIG. 9 is a block diagram of a method for color restoration in accordance with the present disclosure.
Figure 10:
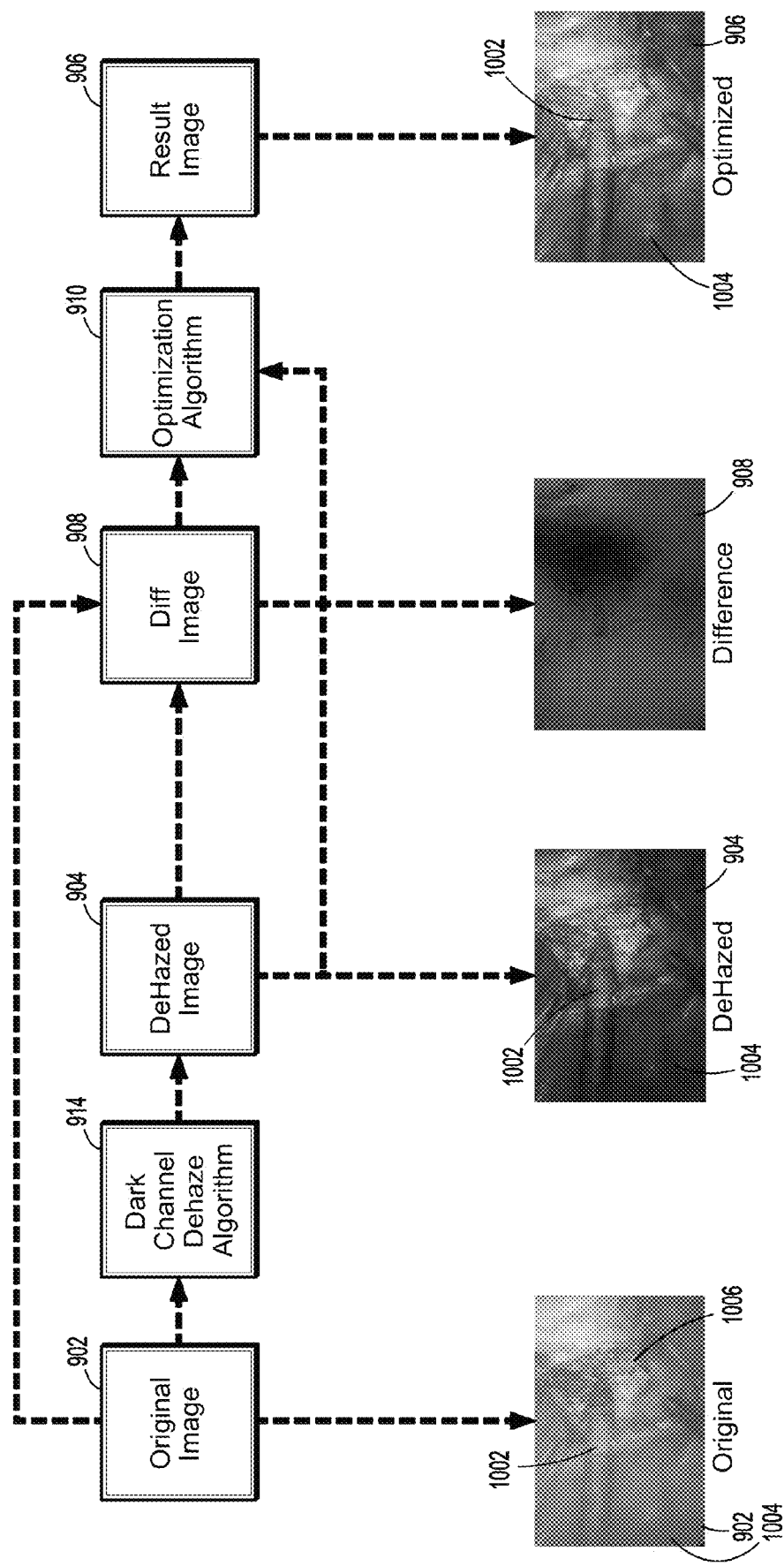
FIG. 10 is a block diagram of a method for color restoration in accordance with the present disclosure.

FIGS. 9 and 10 show exemplary block diagrams of the method for color restoration described in the previous sections. FIG. 10 shows an image 902 with haze captured during a surgical procedure using the endoscope system 1. For example, during an endoscopic procedure, a surgeon may cut tissue 1004 with an electrosurgical instrument 1002. During this cutting, haze 1006 may be generated. This haze 1006 would be captured in the image 902.

FIG. 10 shows a dehazed image 904, where the image 902 has been dehazed. The dehazed image 904 may include an electrosurgical instrument 1002 and tissue 1004. Difference image 908 is created by subtracting the HSV dehazed image 904 from the HSV hazy image 902. RGB color-restored image 906 is color-restored using the method of FIG. 7, as described herein. The RGB color-restored image 906 may include an electrosurgical instrument 1002 and tissue 1004.

The operation may start with the access of the image 902 of FIGS. 9-10 during a surgical procedure. Next, the operation dehazes the image as in step 504.

The operation converts the original hazy image 902 from an RGB image to an HSV image, as in step 702 of FIG. 7. The operation also converts the dehazed image 904 from an RGB image to an HSV image, as in step 704 of FIG. 7. The operation creates a difference image 908 (FIG. 10) by subtracting the HSV dehazed image 904 from the HSV hazy image 902, as in step 706, and feeds this difference image into a pre-trained neural network 910, as in step 708 of FIG. 7, to provide a HSV adjustment image, which contains hue and saturation adjustment values 912 for adjusting the HSV dehazed image 904.

Next, as in step 710, the operation adds the hue and saturation values of the HSV adjustment image to the HSV dehazed image to provide an HSV restored image 906. The operation then converts the restored image 906 from HSV into RGB, as in step 712.

Figure 11:
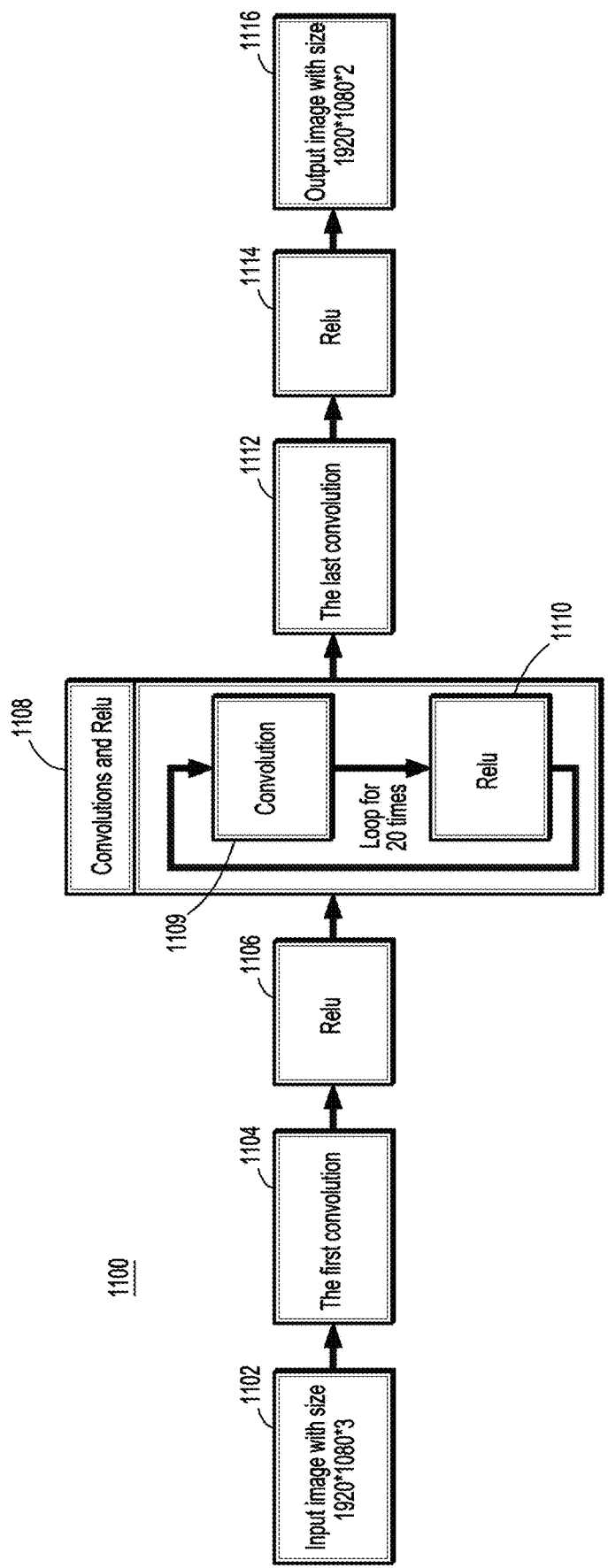
FIG. 11 is an exemplary neural network structure in accordance with the present disclosure.

With reference to FIG. 11, a neural network structure 1100 in accordance with aspects of the present disclosure is shown. In various embodiments, the neural network structure 1100 may include a number of convolution layers, with each including a number of inputs and outputs. For example, a first convolution layer 1104 may include 3 input channels and 16 output channels, and can have the kernel, stride, and padding features in the table below. It is contemplated that during the training process the neural network will find the actual value for the kernel. Persons skilled in the art will understand the operations of a convolutional neural network and of the convolution layers therein. For example, persons skilled in the art will understand that a kernel/filter is convolved with portions of the input for each channel to provide an output matrix/feature map, with the filter moving across the input based on the stride and being applied at edges based on the padding. It is contemplated that different size kernels/filters may be used for different applications, for example, 3×3, 5×5, 7×7×, or 9×9. Other aspects of a convolutional neural network are not explicitly described herein, but would be understood by person skilled in the art, such as pooling.

TABLE 1

First Convolution Layer

| | |
|---|---|
| Input image size | 1920*1080 |
| Input channels | 3 |
| Output image size | 1920*1080 |
| Output channels | 16 |
| Kernel size | 5 |
| Stride | 1 |
| Padding | 2 |

In various embodiments, the HSV difference image D_HSV 1102 is input to the first convolution layer 1104 of the neural network structure 1100. For example, the HSV difference image D_HSV 1102 may be a size of 1920×1080 pixels, with each pixel having 3 parameters—hue, saturation, and value. Accordingly, the three inputs to the first convolution layer correspond to the hue, saturation, and value parameters, and each input is a 1920×1080 set of such values. Persons skilled in the art will recognize the techniques for entering such an input to a convolutional neural network.

In various embodiments, the output of the first convolution layer 1104 includes 16 outputs, which are input into rectified linear unit (ReLU) 1106 activation functions, which persons skilled in the art will understand. In summary, each ReLU unit converts negative values in the output to a zero but leaves the non-negative values unchanged. In various embodiments, the outputs of the ReLU 1106 are input to a middle convolution layer 1108, which can receive 16 inputs and provide 16 outputs. Each input would be a feature map resulting from the first convolutional layer. In the illustrated embodiment, the middle convolution layer 1108 may perform iterative convolutions 1109 and ReLU 1110, as illustrated in FIG. 11, and have the following kernel (e.g., 5×5), stride, and padding parameters. In various embodiments, the activation function may include a ReLU function, a tan h function and/or a sigmoid function. In various embodiments, the number of iterations can be twenty iterations or can be another number of iterations.

TABLE 2

Middle Convolution Layer

| | |
|---|---|
| Input image size | 1920*1080 |
| Input channels | 16 |
| Output image size | 1920*1080 |
| Output channels | 16 |
| Kernel size | 5 |
| Stride | 1 |
| Padding | 2 |

In various embodiments, the output of the middle convolution layer 1108 may be input into a last convolution layer 1112. For example, the last convolution layer may include 16 input channels and include 3 output channels corresponding to hue, saturation, and value parameters, and can operate according to the configuration in the table below. In various embodiments, the last convolution may be input into a ReLU 1114 resulting in a saturation and hue adjustment image F_HSV 1116.

TABLE 3

Last Convolution Layer

| | |
|---|---|
| Input image size | 1920*1080 |
| Input channels | 16 |
| Output image size | 1920*1080 |
| Output channels | 3 |
| Kernel size | 5 |
| Stride | 1 |
| Padding | 2 |

Accordingly, described herein are systems and methods for training and applying a neural network in connection with color restoration. Although dehazing is used as an example herein, color change can result from other types of image processing, and the color restoration aspects described herein can be applied to other types of image processing as well. Additionally, even though the color restoration described herein utilizes HSV color space to determine hue and saturation adjustments, other color spaces can be used and other types of parameters can be used for color adjustment. Additionally, the convolutional neural network disclosed herein is exemplary and does not limit the scope of the present disclosure. Other configurations and other types of neural networks are contemplated to be within the scope of the present disclosure.

The embodiments disclosed herein are examples of the present disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)." The term "clinician" may refer to a clinician or any medical professional, such as a doctor, nurse, technician, medical assistant, or the like, performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (for example, stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the present disclosure. Accordingly, the present disclosure is intended to embrace all such alternatives, modifications and variances. The embodiments described with reference to the attached drawing figures are presented only to demonstrate certain examples of the present disclosure. Other elements, steps, methods, and techniques that are insubstantially different from those described above and/or in the appended claims are also intended to be within the scope of the present disclosure.

What is claimed is:

1. A method for color restoration in images comprising:
   accessing an image of an object;
   processing the image based on an image processing operation to provide a processed image, wherein the image processing affects color of the object;
   determining color adjustment parameters using a trained neural network, wherein an input to the trained neural network is based on the image and the processed image, and further based on combining an RGB haze-free image dataset with an RGB haze dataset, wherein combining includes determining a weighted combination by: image in the RGB haze dataset*coeff+image in the RGB haze-free image dataset*(1−coeff), wherein the coeff is a value between 0 and 1;
   restoring color in the processed image based on the color adjustment parameters to produce a color-restored image; and
   displaying the color-restored image on a display device.

2. The method of claim 1, wherein the image processing operation includes a dehazing operation to dehaze the image, wherein the dehazing operation includes:
   determining a dark channel matrix of the image;
   estimating an atmospheric light component for the image;
   determining a transmission map based on the atmospheric light component and the dark channel matrix; and
   dehazing the image based on the transmission map to provide the processed image.

3. The method of claim 1, wherein the image is an RGB image, and wherein the processed image is an RGB processed image.

4. The method of claim 3,
   wherein determining the color adjustment parameters includes:
      converting the RGB image to an HSV image,
      converting the RGB processed image to a HSV processed image,
      subtracting the HSV image from the HSV processed image to provide an HSV difference image,
      inputting the HSV difference image to the trained neural network, and
      obtaining an HSV adjustment image as an output of the trained neural network, the HSV adjustment image including the color adjustment parameters, and
   wherein restoring color in the processed image includes:
      adding a hue channel and a saturation channel of the HSV adjustment image to the HSV processed image to provide an HSV color-restored image; and
      converting the HSV color-restored image to RGB to provide the color-restored image.

5. The method of claim 3, further comprising training the neural network, the training including:
   accessing the RGB haze-free image dataset having haze-free images;
   accessing the RGB haze dataset having images of haze on a dark background;
   combining the RGB haze-free image dataset with the RGB haze dataset to provide an RGB hazy image dataset;
   dehazing images in the RGB hazy image dataset to provide an RGB dehazed image dataset;
   converting the RGB dehazed image dataset, the RGB hazy image dataset, and the RGB haze-free image dataset from RGB images to HSV images, to provide an HSV dehazed image dataset, an HSV hazy image dataset, and an HSV haze-free image dataset, respectively;
   determining a difference between images in the HSV dehazed image dataset and corresponding images in the HSV hazy image dataset to provide an HSV difference image dataset; and
   providing the HSV difference image dataset as a training input to the neural network.

6. The method of claim 5, wherein training the neural network further includes decreasing a loss function, the loss function being based on at least a portion of the HSV difference image dataset.

7. The method of claim 6, wherein the loss function is further based on a ground truth, the ground truth being based on a difference between an image of the HSV haze-free image dataset and a corresponding image of the HSV hazy image dataset.

8. The method of claim 5, wherein the neural network includes at least one of a convolutional neural network or a fully connected neural network.

9. The method of claim 8, wherein the convolutional neural network includes:
   a first convolution layer having outputs;

a first rectified linear unit configured to receive outputs of the first convolution layer;
a middle convolution layer configured to receive outputs of the first rectified linear unit;
a middle rectified linear unit configured to receive outputs of the middle convolution layer;
a last convolution layer configured to receive outputs of the middle rectified linear unit; and
a last rectified linear unit configured to receive outputs of the last convolution layer,
wherein the middle convolution layer and the middle rectified linear unit are configured to iterate for a number of iterations.

10. A system for color restoration in images comprising:
a display device;
a processor; and
a memory storing instructions which, when executed by the processor, cause the system to:
  access an image of an object;
  process the image based on an image processing operation to provide a processed image, wherein the image processing affects color of the object;
    determine color adjustment parameters using a trained neural network, wherein an input to the trained neural network is based on the image and the processed image, and further based on combining an RGB haze-free image dataset with an RGB haze dataset, wherein combining includes determining a weighted combination by: image in the RGB haze dataset*coeff+image in the RGB haze-free image dataset*(1−coeff), wherein the coeff is a value between 0 and 1;
  restore color in the processed image based on the color adjustment parameters to produce a color-restored image; and
  display the color-restored image on the display device.

11. The system of claim 10, wherein the image processing operation includes a dehazing operation to dehaze the image, wherein the instructions, when performing the dehazing operation further cause the system to:
  determine a dark channel matrix of the image;
  estimate an atmospheric light component for the image;
  determine a transmission map based on the atmospheric light component and the dark channel matrix; and
  dehaze the image based on the transmission map to provide the processed image.

12. The system of claim 10, wherein the image is an RGB image, and wherein the processed image is an RGB processed image.

13. The system of claim 12, wherein, the instructions, when determining the color adjustment parameters further cause the system to:
  convert the RGB image to an HSV image,
  convert the RGB processed image to a HSV processed image,
  subtract the HSV image from the HSV processed image to provide an HSV difference image,
  input the HSV difference image to the trained neural network, and
  obtain an HSV adjustment image as an output of the trained neural network, the HSV adjustment image including color adjustment parameters, and
  wherein restoring color in the processed image includes:
    add a hue channel and a saturation channel of the HSV adjustment image to the HSV processed image, to provide an HSV color-restored image, and
  convert the HSV color-restored image to RGB to provide the color-restored image.

14. The system of claim 12, wherein the instructions when training the neural network further cause the system to:
  access the RGB haze-free image dataset having haze-free images;
  access the RGB haze dataset having images of haze on a dark background;
  combine the RGB haze-free image dataset with the RGB haze dataset to provide an RGB hazy image data set;
  dehaze images in the RGB hazy image dataset to provide an RGB dehazed image dataset;
  convert the RGB dehazed image dataset, the RGB hazy image dataset, and the RGB haze-free image dataset from RGB images to HSV images, to provide an HSV dehazed image dataset, an HSV hazy image dataset, and an HSV haze-free image dataset, respectively;
  determine a difference between images in the HSV dehazed image dataset and corresponding images in the HSV hazy image dataset to provide an HSV difference image dataset; and
  provide the HSV difference image dataset as a training input to the neural network.

15. The system of claim 14, wherein training the neural network further includes decreasing a loss function, the loss function being based on at least a portion of the HSV difference image dataset.

16. The system of claim 15, wherein the loss function is further based on a ground truth, the ground truth being based on a difference between an image of the HSV haze-free image dataset and a corresponding image of the HSV hazy image dataset.

17. The system of claim 10, wherein the neural network includes at least one of a convolutional neural network or a fully connected neural network.

18. The system of claim 17, wherein the convolutional neural network includes:
  a first convolution layer having outputs;
  a first rectified linear unit configured to receive outputs of the first convolution layer;
  a middle convolution layer configured to receive outputs of the first rectified linear unit;
  a middle rectified linear unit configured to receive outputs of the middle convolution layer;
  a last convolution layer configured to receive outputs of the middle rectified linear unit; and
  a last rectified linear unit configured to receive outputs of the last convolution layer, wherein the middle convolution layer and the middle rectified linear unit are configured to iterate for a number of iterations.

* * * * *